(12) United States Patent
Daste et al.

(10) Patent No.: US 9,474,713 B2
(45) Date of Patent: Oct. 25, 2016

(54) CHEWABLE COMPOSITION FOR ORAL ADMINISTRATION AND PROCESS FOR PREPARING THEREOF

(71) Applicant: SANOFI, Paris (FR)

(72) Inventors: Georges Daste, Paris (FR); Benjamin Derouet, Paris (FR); Marie Renouard, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/767,527

(22) PCT Filed: Feb. 12, 2014

(86) PCT No.: PCT/EP2014/052746
§ 371 (c)(1),
(2) Date: Aug. 12, 2015

(87) PCT Pub. No.: WO2014/124981
PCT Pub. Date: Aug. 21, 2014

(65) Prior Publication Data
US 2015/0374622 A1    Dec. 31, 2015

(30) Foreign Application Priority Data
Feb. 14, 2013  (EP) .................................... 13305172

(51) Int. Cl.
| | |
|---|---|
| *A61K 31/445* | (2006.01) |
| *A23G 3/48* | (2006.01) |
| *A23L 1/30* | (2006.01) |
| *A61K 31/47* | (2006.01) |
| *A61K 9/00* | (2006.01) |
| *A23G 3/36* | (2006.01) |
| *A23L 1/0524* | (2006.01) |
| *A61K 31/192* | (2006.01) |
| *A61K 47/10* | (2006.01) |
| *A61K 47/36* | (2006.01) |

(52) U.S. Cl.
CPC .............. *A61K 9/0056* (2013.01); *A23G 3/364* (2013.01); *A23G 3/48* (2013.01); *A23L 1/0524* (2013.01); *A23L 1/30* (2013.01); *A23L 29/231* (2016.08); *A23L 33/10* (2016.08); *A61K 31/192* (2013.01); *A61K 31/445* (2013.01); *A61K 31/47* (2013.01); *A61K 47/10* (2013.01); *A61K 47/36* (2013.01); *A23V 2002/00* (2013.01)

(58) Field of Classification Search
None
See application file for complete search history.

(56) References Cited

U.S. PATENT DOCUMENTS

| | | |
|---|---|---|
| 2010/0291245 A1 | 11/2010 | Gao et al. |
| 2015/0313885 A1 | 11/2015 | Merillon et al. |

FOREIGN PATENT DOCUMENTS

| | | |
|---|---|---|
| CN | 101628117 A | 1/2010 |
| WO | WO-03/041683 A2 | 5/2003 |
| WO | WO-03/041683 A3 | 5/2003 |
| WO | WO-2007/017905 A1 | 2/2007 |
| WO | WO-2013/015545 A1 | 1/2013 |

OTHER PUBLICATIONS

International Search Report mailed on Feb. 27, 2014, for PCT Application No. PCT/EP2014/052746, filed on Feb. 12, 2014, four pages.

*Primary Examiner* — Samantha Shterengarts
(74) *Attorney, Agent, or Firm* — Morrison and Foerster LLP

(57) ABSTRACT

The present invention relates to chewable compositions for oral administration, said compositions comprising high(methyl)pectin, glycerol and water. Advantageously, the chewable composition can comprise a drug substance. The present invention also concerns a process for preparing the chewable composition and the use of said chewable composition as a medicament.

10 Claims, 1 Drawing Sheet

CHEWABLE COMPOSITION FOR ORAL ADMINISTRATION AND PROCESS FOR PREPARING THEREOF

CROSS-REFERENCE TO RELATED APPLICATIONS

Figure 1:
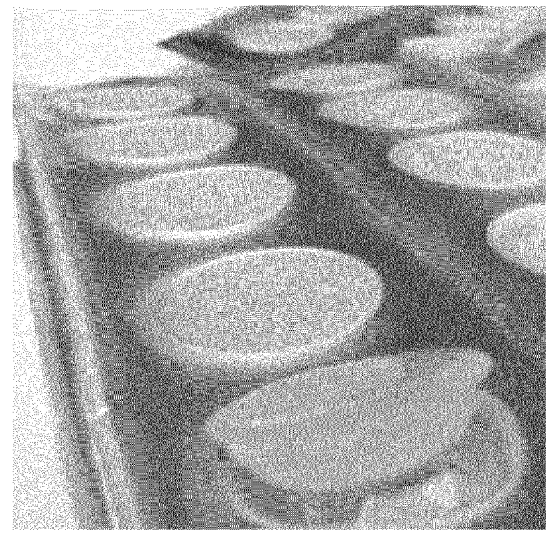

This application is a National Phase application under 35 U.S.C. §371 of International Application No. PCT/EP2014/052746 filed Feb. 12, 2014, which claims priority to European Application No. 13305172.2 filed Feb. 14, 2013, the disclosures of each of which are incorporated herein by reference in their entirety.

The present invention relates to a chewable composition comprising high(methyl)pectin, glycerol and water. Advantageously, the chewable composition can comprise a drug substance. The present invention also concerns a process for preparing the chewable composition and the use of said chewable composition as a medicament.

Because of some properties such as solubility or compressibility, of certain drug substances, it happens that, tablets containing so are big enough. Thus, some patients, especially elderly patients and children, may have difficulty in swallowing the rather large tablet.

Additionally, the administration of a tablet usually requires the ingestion of a liquid in order to facilitate the swallowing. In everyday life, patients do not have always liquids at hand.

These issues can result in poor compliance or non-compliance with a treatment.

Thus, there is still a need for new formulations, suitable for oral administration, which can be convenient for most patients, especially including the elderly and children. In particular, such a formulation should be easy to swallow and preferably be ingested without liquid.

The present invention thus relates to a composition for oral administration comprising:
- 0.5-3.5% wt, preferably 1-3% wt, of high(methyl)pectin,
- 40-70% wt, preferably 50-68% wt, of glycerol,
- 16-30% wt, preferably 20-29% wt, of water,
- 0-2.5% wt, when present, preferably 0.1-1.5% wt, of at least one surfactant,
- 1.5-40% wt, preferably 2-30% wt, of at least one another ingredient selected from the group consisting of: sugar substitutes, flavouring agents, colouring agents and/or active substances, the weight percentages being relative to the total weight of the composition and the pH of the composition being within the range of about 2.8 to about 3.2.

It should be noted that throughout the present application, ranges are intended limits inclusive.

Pectin is represented by general formula (II) below:

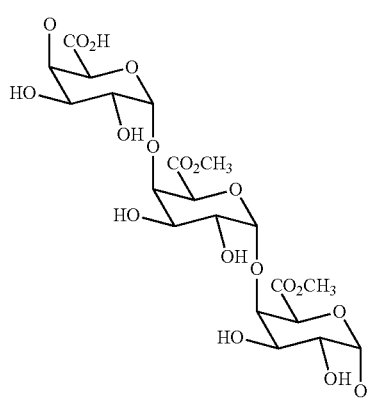

Formula (II)

In pectin, which is extracted normally, more than 50% of the acid units are esterified. This pectin is usually classified and known as "high methyl ester pectin" or "high(methyl) pectin". The percentage of ester groups is known as the degree of esterification (DE). Preferably, according to the invention, high(methyl)pectin has a DE from about 50 to about 80, more preferably, from about 65 to about 75. High(methyl)pectin is an important ingredient of the composition. Indeed, high(methyl)pectin allows one to obtain a composition, which, once formed, can be grasped. Additionally, with high(methyl)pectin, the gelling of the composition is easily controlled, occurs rapidly, i.e. in less than 2 hours and doesn't require to heat the composition at temperature above 90° C., avoiding any potential degradation of other ingredients, such as a drug substance, which may be contained herein.

In the composition according to the invention, glycerol is introduced as a sort of co-agent of the pectin, which allows, with the presence of water and the adjustment of the pH, the gelling of the composition. Additionally, the presence of glycerol avoids the use of sucrose in the compositions, sucrose being caloric and cariogenic. One particular advantage of the composition according to the invention is that said composition is sugar free.

Preferably, water introduced into the composition is purified water according to the U.S. and E.U. pharmacopeias.

The composition according to the invention may comprise at least one surfactant, the presence of which is only required in some particular embodiments. For example, the presence of the surfactant may be required depending on the composition preparation process.

When present, the surfactant is preferably a non-ionic surfactant. Advantageously, the surfactant is chosen among the group consisting of: ethylene propylene oxide copolymers, such as those sold under the trademark POLOXAMER, polysorbates, such as those sold under the trademark TWEEN. Preferably, the surfactant is a polyoxyethylene (20) sorbitan monooleate (or polysorbate 80) such as sold under the trade name TWEEN 80.

Additionally, the composition according to the invention may comprise at least one another ingredient selected in the group consisting of: sugar substitutes, flavouring agents, colouring agents and/or actives substances.

By "active substance", it is meant a drug substance, optionally with at least one pharmaceutical excipient.

The drug substance is more particularly a molecule (which may be in a salt form) intended to treat at least one disease and/or cure at least one symptom. This drug substance is introduced in the composition at a dose corresponding to the usual posology of said drug substance.

As an example, the drug substance can be selected among the group consisting of:
antalgic agent, analgesic agent, antipyretic agent, molecules able to treat cold and cough (in particular antitussive agent, decongestant agent and/or expectorant agent), molecules able to treat allergies (antihistamine), antispasmodic agent, antidiarrheal agent, anti-inflammatory agent (such as non-steroidal anti-inflammatory drug (NSAID)), vasodilator agent, anti-infectious agent, antiviral agent, anti-cancer agent, anxiolytic agent, antiepileptic agent, hypertensor agent, anti-hypertensive agent, antimigraine agent, myorelaxant agent, diuretic agent, or combination thereof.

Preferably, said drug substance is selected among the group consisting of:

Diphenhydramine, Chlorpheniramine, Loratidine, Cetirizine, Pseudoephedrine, Guaifenesin, Dextromethorphan, Naproxen, Aspirin, Acetaminophen, Ibuprofen, Ketoprofen, Drotaverine, Codeine and or combination thereof.

The drug substance can also be selected among the group consisting of molecules having prophylactic or nutraceutical activities such as:

Vitamins (A, K, D, E, C, B1, B12) or multivitamin composition, minerals (such as calcium salts), oestrogen, unsaturated fatty acids, flavonoids, phytosterol, plant extract, or other, and combination thereof.

The drug substance may be added to the composition optionally with at least one pharmaceutical excipient.

Preferably, the pharmaceutical excipient is selected among the group consisting of:

excipients able to enhance the solubility of the drug substance. As an example, cyclodextrin can complex with the drug substance and enhance its solubility;

excipients able to buffer the drug substance, such as a phosphate buffer at pH 6.2;

excipients able to coat the drug substance for enteric resistance. As an example, enteric-resistant polymers can be chosen among polymethacrylates (such as those sold under the trade name Eudragit® L), cellulose esters such as hypromellose acetate succinate (HPMCAS) and/or cellulose acetate phthalate (CAP), and/or polyvinyl derivatives such as polyvinyl acetate phthalate (PVAP), etc.;

excipients able to coat the drug substance for taste-masking. As an example, taste-masking excipients can be chosen among hydroxypropyl methylcellulose (HPMC), polyvinylpyrrolidone (PVP), polyethylene glycol (PEG), polymethacrylate, ethylcellulose (EC), stearic acid, etc.

When the composition according to the invention comprises at least one active substance, this composition is more particularly a pharmaceutical composition.

By sugar substitute, it is meant a food additive that replicates the taste of sugar. Preferably, said sugar substitutes are artificial sweeteners such as sucralose, saccharine and/or potassium acesulfame.

The flavouring agents are preferably selected in the group consisting of lime, lemon, strawberry and apple.

By colouring agents, it is meant dyes, lakes and/or opacifying agents. Examples of such colouring agents are red iron oxide, yellow iron oxide, $TiO_2$, carmine E120, FD&C blue no. 1 Aluminium Lake, etc.

To gel the composition, the pH of the composition must be adjusted within a range of about 2.8 to about 3.2, preferably, within the range of about 2.9 to about 3.1. Said adjustment is performed by adding an acid to the composition. Preferably, the acid is chosen among the group consisting of citric acid, tartaric acid, phosphoric acid and lactic acid, and is more preferably, citric acid.

The composition according to the invention has a water activity of less than 0.61.

The <<water activity>> represents the water availability (i.e. free water) which can be used by the microorganisms for their growth within the sample. The water activity may be measured by methods known in the art.

Preferably, the water activity is less than 0.60, more preferably, less than 0.59 and still more preferably less than 0.58. This low water activity is of particular interest because it renders the addition of preservatives to the composition, such as parabens, unnecessary.

It may be noted that once gelled, the composition according to the invention forms a solid which is chewable. Moreover, for people having few or no teeth, said chewable composition can also be sucked.

This is of particular interest for a pharmaceutical composition, can be easily ingested by all patients, particularly by the elderly and the children. Additionally, the pharmaceutical composition may also have an agreeable appearance and a pleasant taste:

the taste of the composition can be modified by the addition of suitable sugar substitute(s) and flavouring agent(s), and colouring agent(s) may render the chewable composition more attractive.

All these features make the compliance with the treatment easier for the patient.

The pharmaceutical composition according to the invention can be used as a medicament, depending on the drug substance contained herein.

The compositions according to the invention, under solid form, can be divided into units. Preferably, in case of a pharmaceutical composition, each unit comprises a dose of drug substance.

As mentioned above, the compositions according to the invention may form units, which are graspable. In particular, a 1.5 g unit of the composition has a hardness comprised in the range from 30 g to 300 g, preferably from 40 g to 250 g, more preferably from 50 g to 200 g, when measured by a texture analyser. Measurements by a texture analyser are known in the art. An example of such a measurement is more specifically described in the examples below. It has been noticed that the hardness of the units depends on the soluble or suspension form of the ingredients contained in the composition. More particularly, an active substance in a suspension form introduces particles in the composition, which, one gelled, stiffen said gel.

The present invention further relates to a process for preparing a composition and more particularly a pharmaceutical composition according to the invention, comprising the following steps:

(i) Mixing glycerol, water, optionally with the active substance(s) and/or the surfactant(s), (ii) After heating, adding the high(methyl)pectin, (iii) Adding the sugar substitute(s), flavouring agent(s) and/or colouring agent(s), if any, (iv) Heating the resulting mixture of step (ii) to a temperature ranging from about 60° C. to about 90° C., preferably at a temperature of about 70° C., (v) Adjusting the pH with an acid, (vi) Forming and cooling the composition until gelling occurs.

Advantageously, the addition of the high(methyl)pectin of step (ii) is performed after heating the mixture of step (i) to a temperature within the range of about 35° C. to 45° C., preferably at about 40° C.

Preferably, in step (v), the pH is adjusted with citric acid, tartaric acid, phosphoric acid and/or lactic acid, and more preferably, with citric acid.

In a first preferred embodiment, the forming step is performed by pouring the composition into moulds. Advantageously, the moulds may be further lined up to form a blister pack, which may then be thermally sealed.

In a second preferred embodiment, the forming step is performed by deposition of a drop of the composition on a cooled belt. The drops solidify and cool as they travel along with the belt. The solidified units are then discharged at the end of the belt and collected. The cooled belt may be made of steel or another suitable material.

Figure 2:
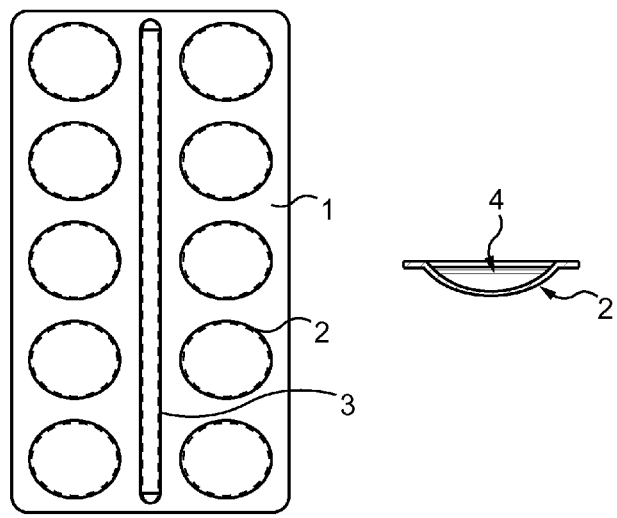

The present invention is further illustrated by the following examples, which are not to be construed in any way as limiting, with reference to:

FIG. 1, which is a photo of a mould filled with the composition according to the invention, and FIG. 2, which is a diagram of the mould used to prepare the units of composition in example 1.

EXAMPLE 1

Composition Comprising Fexofenadine

1. Composition

A pharmaceutical composition according to the invention was prepared with the following ingredients:

| Ingredient | Grade or trademark | Quantity | % wt |
|---|---|---|---|
| Fexofenadine | Anhydrous fexofenadine hydrochloride | 16.0 g | 4.0%* |
| β-cyclodextrin | Kleptose ®BetaCyclo-Dextrin | 67.6 g | 16.9%* |
| High(methyl)pectin | Genu ®Pectin type USP-H | 8.0 g | 2.0%* |
| Glycerol | Anhydrous (98-101.1%) | 215.6 g | 53.9%* |
| Water | Purified water | 88.0 g | 22.0%* |
| Flavouring agent | Lime flavour | 2.0 g | 0.5%* |
| Sugar substitute | Sucralose | 2.0 g | 0.5%* |
| Surfactant | Polysorbate 80 (TWEEN 80) | 0.8 g | 0.2%* |
| Acid | Citric acid 10% w/w** | Qs*** | pH = 3 |

*The percentage of each ingredient is the weight percentage with respect to the total weight of the composition.
**w/w: weight/weight
***Qs: quantum satis.

2. Preparation Process

The preparation of the pharmaceutical composition is carried out as follows.

In this example, the active substance is:
fexofenadine hydrochloride with its pharmaceutical excipient, β-cyclodextrin.

The aim of the first steps of the process is to solubilize and disperse the fexofenadine: 67.6 g of β-cyclodextrin is mixed with 44 g of water to form a pasty mixture. Then, 12 g of fexofenadine is added to the mixture, followed by 31 g of water, the addition of the water having the purpose of avoiding the hardening of the mixture. Finally, the rest of fexofenadine is added, followed by the rest of water.

215.6 g of glycerol and 0.8 g of surfactant are then added to the mixture and mixed. The mixture is heated at 40° C. When the mixture has reached 40° C., 8 g of high(methyl)pectin is added to the mixture.

2 g of sucralose and 2 g of lime flavour are added to the mixture, which is then heated to a temperature of 70° C. The pH is adjusted with a solution of citric acid 10% w/w.

The resulting mixture is the pharmaceutical composition according to the invention. Said composition is then poured into plastic or metal-laminated moulds.

An example of blister pack is illustrated in FIG. 2. In this figure, the blister pack 1 comprises two parallel rows of cavities 2 and is reinforced by a central rib 3. Each cavity is cup-shaped. The maximum diameter of the cup (at the surface of the blister pack 1) is about 20 mm and its depth is about 6.5 mm.

Each cavity is filled with 1.5 g (corresponding to a dose of 60 mg of fexofenadine hydrochloride) of the pharmaceutical composition 4, which is liquid. The blister pack is then thermally sealed with a foil cover sheet, and the pharmaceutical composition is cooled until the composition gels.

Once gelled, the pharmaceutical composition according to the invention can be easily turned out of the moulds to form a moulded unit and is easily grasped, as shown in FIG. 1.

3. Water Activity

The pharmaceutical composition according to the invention does not require the use of any preservatives. In particular, the addition of parabens can be avoided. This feature can be evidenced by measuring the water activity of the pharmaceutical composition according to the invention.

The water activity is measured by using a Rotronic Hygrolab device. This measurement is not carried out on an entire moulded unit, but on a sample portion of said unit, the sample having the following dimensions: 20 mm in diameter (x) 2-3 mm in thickness. This portion is sliced from the moulded unit. The sample is then introduced into the measuring cell. After a short equilibrium time, the value can be read.

The water activity as measured is: 0.58. This result is below a water activity of 0.61, which represents the upper limit, above which a preservative is required.

4. Hardness

As mentioned above, the moulded units are easily grasped. To evaluate this feature, the hardness of said units has been measured with a texture analyser.

Method:

The texture analyser is a TA.XT.plus Texture Analyser, from Stable Micro Systems® equipped with a 6 mm diameter cylinder probe with a 5 kg load cell.

The parameters of the texturometer are as follows:
Mode: Measure force in compression
Test speed=1 mm/s
Distance=1 mm
Trigger type=Auto−5.0 g The measurement is performed on a sample constituted by a moulded unit. This moulded unit is positioned so as the surface which was in contact with the cup of the blister pack is facing upwards. Once the probe has touched said surface of the sample, it penetrates it until a depth of 1 mm is reached. At this depth, the load is measured and this value represents the hardness of the sample. To assess the reproducibility of the measurement, 10 samples are tested.

The hardness measured is comprised in the range from 50 to 100 g. It has been determined that a unit having a hardness below 30 g is not graspable. This confirms that the moulded units of the pharmaceutical composition according to the invention are graspable.

EXAMPLE 2

Composition Comprising Ibuprofen

1. Composition

A pharmaceutical composition according to the invention was prepared with the following ingredients:

| Ingredient | Grade or trademark | Quantity | % wt |
|---|---|---|---|
| Ibuprofen | Ibuprofen acid | 3.3 g | 6.7%* |
| High(methyl)pectin | Genu ®Pectin type USP-H | 1.0 g | 2.0%* |

-continued

| Ingredient | Grade or trademark | Quantity | % wt |
|---|---|---|---|
| Glycerol | Anhydrous (98-101.1%) | 32.1 g | 64.2%* |
| Water | Purified water | 13.5 g | 26.9%* |
| Surfactant | Polysorbate 80 (TWEEN 80) | 0.1 g | 0.2%* |
| Acid | Citric acid 10% w/w** | Qs*** pH = 3 | |

*The percentage of each ingredient is a weight percentage given on the total weight of the composition.
**w/w: weight/weight
***Qs: quantum satis.

2. Process of Preparation

The preparation of the pharmaceutical composition is conducted as follows.

The active substance, ibuprofen acid (3.3 g), is first mixed with water (13.5 g) and surfactant (0.1 g). 32.1 g of glycerol are progressively added to the mixture and mixed.

The mixture is heated at 40° C.

When the mixture has reached 40° C., 1 g of high(methyl) pectin is added to the mixture.

The mixture is then heated to a temperature of approximately 70° C. pH is adjusted with a solution of citric acid 10% w/w to reach a value of approximately 3.

The resulting mixture is poured into moulds (see example 1). The pharmaceutical composition is then in solid form units of 1.5 g. Each unit comprises a dose of ibuprofen acid of 100 mg.

3. Water Activity

After gelling, the gelled compositions are turn out of the moulds and the water activity is measured. This measurement is made according to the protocol described in example 1.

Water activity (as measured): 0.49

4. Hardness

The hardness is measured according to the protocol described in example 1. To assess the repeatability of the measure, 10 samples are tested.

Hardness measured is comprised in the range from 150 to 250 g. This hardness, which is greater than the hardness of the fexofenadine units, may be explained by the fact that ibuprofen is in suspension in the gel, the presence of the ibuprofen particles resulting in a stiffening of the gel.

EXAMPLE 3

Composition Comprising Drotaverine

1. Composition

A pharmaceutical composition according to the invention was prepared with the following ingredients:

| Ingredient | Grade or trademark | Quantity | % wt |
|---|---|---|---|
| Drotaverine | Drotaverine HCl | 2.7 g | 2.7%* |
| High(methyl)pectin | Genu ®Pectin type USP-H | 2.0 g | 2.0%* |
| Glycerol | Anhydrous (98-101.1%) | 67.5 g | 67.5%* |
| Water | Purified water | 27.6 g | 27.6%* |
| Surfactant | Polysorbate 80 (TWEEN 80) | 0.2 g | 0.2%* |
| Acid | Citric acid 10% w/w** | Qs*** pH = 3 | |

*The percentage of each ingredient is a weight percentage given on the total weight of the composition.
**w/w: weight/weight
***Qs: quantum satis.

2. Process of Preparation

The preparation of the pharmaceutical composition is conducted as follows.

The active substance drotaverine hydrochloride (2.7 g) is first mixed with 19.3 g of water and 0.2 g of polysorbate 80. The remaining quantity of water (8.3 g) is then added to the mixture, followed by the progressive addition of 67.5 g of glycerol under mixing conditions.

The mixture is heated at 40° C.

When the mixture has reached 40° C., 2 g of high(methyl) pectin is added to the mixture.

The mixture is then heated up to a temperature of approximately 70° C. pH is adjusted with a solution of citric acid 10% w/w to reach a value of approximately 3.

The resulting mixture is poured into moulds. The pharmaceutical composition is then in solid form units of 1.5 g. Each unity comprises a dose of drotaverine hydrochloride of 40 mg.

3. Water Activity

After gelling, the gelled compositions are turn out of the moulds and the water activity is measured. This measurement is made according to the protocol described in example 1.

Water activity (as measured): 0.56

4. Hardness

The hardness is measured according to the protocol described in example 1. To assess the repeatability of the measure, 10 samples are tested.

Hardness measured is comprised in the range from 50 to 75 g.

The invention claimed is:

1. A composition for oral administration comprising:
   0.5-3.5% wt of high(methyl)pectin;
   40-70% wt of glycerol;
   16-30% wt of water;
   0-2.5% wt of at least one surfactant; and
   1.5-40% wt of at least one other ingredient selected from the group consisting of sugar substitutes, flavoring agents, coloring agents and active substances,
   wherein the weight percentages are relative to the total weight of the composition and the pH of the composition is within the range of about 2.8 to about 3.2.

2. The composition of claim 1, wherein the composition has a water activity of less than 0.61.

3. The composition of claim 1, wherein the pH of the composition is adjusted with an acid.

4. The composition of claim 1, wherein the composition is chewable.

5. A pharmaceutical composition comprising the composition of claim 1, comprising at least one active substance, wherein said active substance is a drug substance; and optionally further comprising at least one pharmaceutical excipient.

6. A process for preparing the composition of claim 1, comprising the steps of:
   (i) mixing glycerol, water, the active substance(s), where present, and the surfactant(s);
   (ii) heating the mixture of step (i);
   (iii) adding the high(methyl)pectin;
   (iv) adding, where present, the sugar substitute(s), flavoring agent(s) and coloring agent(s);
   (v) heating the resulting mixture of step (iii) or, where present, step (iv) to a temperature ranging from 60° C. to 90° C.;
   (vi) adjusting the pH with an acid; and
   (vii) forming and cooling the composition until gelling occurs.

7. The process of claim 6, wherein the heating of step (ii) is performed within the range of 35° C. to 45° C.

8. The process of claim 6, wherein the pH is adjusted with citric acid.

9. The process of claim 6, wherein the forming step is performed by pouring the composition into molds.

10. The process of claim 6, wherein the forming step is performed by deposition of a drop of the composition on a cooled belt.

* * * * *